United States Patent
Bonnett (10) Patent No.: US 11,291,819 B2
(45) Date of Patent: Apr. 5, 2022

(54) CUSTOMIZABLE TATTOO STAMP FOR PERMANENT MULTICOLOR TATTOO ON SKIN

(71) Applicant: BlinkInk LLC, Pittsburgh, PA (US)

(72) Inventor: Thane Bonnett, Pittsburgh, PA (US)

(73) Assignee: BlinkInk LLC, Pittsburgh, PA (US)

( * ) Notice: Subject to any disclaimer, the term of this patent is extended or adjusted under 35 U.S.C. 154(b) by 91 days.

(21) Appl. No.: 16/849,490

(22) Filed: Apr. 15, 2020

(65) Prior Publication Data
US 2020/0330740 A1    Oct. 22, 2020

Related U.S. Application Data

(60) Provisional application No. 62/834,620, filed on Apr. 16, 2019.

(51) Int. Cl.
*A61M 37/00*    (2006.01)

(52) U.S. Cl.
CPC .... *A61M 37/0084* (2013.01); *A61M 37/0015* (2013.01); *A61M 2037/003* (2013.01); *A61M 2037/0053* (2013.01); *A61M 2037/0061* (2013.01)

(58) Field of Classification Search
CPC .......... A61M 37/0084; A61M 37/0015; A61M 2037/003; A61M 2037/0061; A61M 2037/0053; A61M 37/0076
See application file for complete search history.

(56) References Cited

U.S. PATENT DOCUMENTS

| | | | |
|---|---|---|---|
| 3,039,467 A * | 6/1962 | Stone | A61M 37/0076 606/116 |
| 6,312,124 B1 | 11/2001 | Desormeaux | |
| 6,565,532 B1 | 5/2003 | Yuzhakov et al. | |
| 7,141,034 B2 | 11/2006 | Eppstein et al. | |
| 7,627,938 B2 | 12/2009 | Kim et al. | |
| 10,617,857 B1 * | 4/2020 | Phillips | A61M 37/0084 |
| 2004/0267283 A1 | 12/2004 | Mavor et al. | |
| 2006/0264804 A1 | 11/2006 | Karmon et al. | |
| 2007/0032846 A1 | 2/2007 | Ferren et al. | |

(Continued)

FOREIGN PATENT DOCUMENTS

| | | |
|---|---|---|
| CN | 101507857 A | 8/2009 |
| CN | 105943365 A | 9/2016 |

(Continued)

*Primary Examiner* — Amber R Stiles
(74) *Attorney, Agent, or Firm* — Penn State Law IP Clinic (57) ABSTRACT

The present invention is a big step forward from the traditional method of drawing a tattoo on human skin, which requires a skilled artist to use the tattoo machine comprising a single needle to deposit ink single injection by single injection. The disclosed invention comprises of a customizable needle substrate, a charging unit, an image processor unit, an ink roller and may be an injection device, to print a permanent multicolor image on the human skin using an instantaneous method of injecting the ink at desired depth in a human skin, resulting in an image or tattoo on the human skin. The method also causes less pain in comparison to the traditional method of tattoo making, as the process is relatively quick. Furthermore, the disclosed invention reduces the dependency on a skilled artist to draw a tattoo on the human skin.

10 Claims, 9 Drawing Sheets

(56) References Cited

U.S. PATENT DOCUMENTS

| | | |
|---|---|---|
| 2010/0121307 A1 | 5/2010 | Lockard et al. |
| 2011/0237925 A1 | 9/2011 | Yue et al. |
| 2012/0244316 A1 | 9/2012 | Dobler et al. |
| 2013/0338626 A1 | 12/2013 | Ferren et al. |
| 2016/0000646 A1* | 1/2016 | Scherkowski ..... A61H 23/0254 601/108 |
| 2017/0055499 A1* | 3/2017 | Peppou ................ A01K 11/005 |

FOREIGN PATENT DOCUMENTS

| | | |
|---|---|---|
| CN | 108325065 A | 7/2018 |
| KR | 100873642 B1 | 12/2008 |
| KR | 101412574 B1 | 6/2014 |
| KR | 20150001944 A | 1/2015 |
| WO | WO2008053481 A1 | 5/2008 |
| WO | WO2008085758 A2 | 7/2008 |
| WO | WO2011089435 A2 | 7/2011 |
| WO | WO2018033325 A1 | 2/2018 |

* cited by examiner

CUSTOMIZABLE TATTOO STAMP FOR PERMANENT MULTICOLOR TATTOO ON SKIN

CROSS REFERENCE SECTION

This application claims the benefit of U.S. Prov. No. 62/834,620 filed Apr. 16, 2019 which is incorporated herein by reference.

BACKGROUND OF THE INVENTION

The current system of making a tattoo on a human skin requires a skilled artist to use the tattoo machine to deposit the ink, which is a labor intensive and time-consuming process. There exists a need for a tattoo device available that can deliver a tattoo into the human skin with multiple needles. The tattoo Stamp is the first device that prints an entire image into the skin at once. The technology center to this invention is the needle-substrate unit onto which a permanent tattoo ink is printed, coating an array of needles with a pattern of ink, and then transferring that pattern into the skin.

SUMMARY OF THE INVENTION

The invention relates to a tattoo stamp system that prints a desired image into the skin at once causing minimal pain, as the process is extremely quick, taking seconds to give a tattoo instead of a half hour or more in the traditional tattoo making method, in which a needle goes over the skin repeatedly to make the tattoo. The disclosed invention comprises a customizable needle-substrate unit, which may comprise an array of individual movable blocks held together under compression, each including one or more closely spaced needles in a desired pattern where each needle constitutes a pixel of an image, allowing for permanent tattoo ink to be transferred into the skin in the desired pattern, which ultimately creates a permanent tattoo. In sum, the invention is an improvement in methods and system related to the tattoo making method.

In some embodiments the customizable tattoo stamp system utilizes an injection device, which can operate on pneumatic, mechanical, or electrostatic principles to press against the rear of the blocks to press the needles into the skin.

In some embodiments the customizable tattoo stamp system comprises of a customizable needle-substrate unit, a charging unit, an image processor unit, and may include an injection device depending on the principle used for injecting the permanent tattoo ink into the skin. These components form part of the multi-step tattooing process. The customizable needle-substrate unit can be manufactured using hard or soft material depending on the location where the tattoo is to be made, while the needles must be rigid. The needle-substrate unit itself can be manufactured in the shape of the desired image, or it can be a uniform array of needles. The tracing of the image onto the needle-substrate unit starts with positively charging the needle-substrate unit using the corona wire and the power source. An image processing unit can comprise of a microprocessor, laser and a mirror or a computer numerical control laser and a microprocessor, depending upon the method being employed to trace a 2-D image onto the custom needle pad. The image on the customizable needle pad is transferred onto the human skin using an injection device which can operate on pneumatic, mechanical and electrostatic principle.

In some embodiments the customizable tattoo stamp system comprises: a customizable needle-substrate unit made up of a hard substance or a soft substance or a combination thereof, onto which the permanent tattoo ink is printed using the ink roller; a charging unit comprising of a corona wire and a power source; an image processor unit, which can use either of the two methods to trace the image on the custom needle-substrate unit, one which consists of a microprocessor, a laser, and a mirror, and the other which consists of a microprocessor and CNC laser; an injection device, which can work using the pneumatic, mechanical, or electrostatic principles to transfer the permanent tattoo ink into the skin, which ultimately creates a permanent tattoo. In one aspect. the method of coating comprises using an array of needles with a pattern of permanent tattoo ink and transferring the pattern into the skin. In one aspect, the customizable needle substrate is charged using a corona wire and a power source. In one aspect, the method of claim 2 wherein a laser, microprocessor, and a mirror or CNC and the microprocessor are used to trace a 2-D image onto the needle pad. In one aspect, the method comprises a positively charged ink roller is used to coat an array of needles with a pattern of permanent tattoo ink. In one aspect, the method comprises the image on the customizable needle pad is transferred into the skin using an injection device which can operate on pneumatic, mechanical and electrostatic principle.

In some embodiments the method of tattooing a user, comprises: inserting an array of needles into said user's skin and transferring permanent tattoo ink into said user's skin wherein said insertion and withdrawal of the said array of needles is fairly quick in comparison to the traditional tattoo machine, resulting in less pain for said user as compared to said user receiving a tattoo of similar size using a traditional single needle method.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 is an exemplary illustration of the six steps of the tattooing process with the tattoo stamp system.

FIG. 6 is an exemplary illustration of a tattoo stamp method that relies on movable blocks, where each block may hold a multitude of needles.

FIG. 7 is an exemplary illustration of a tattoo stamp method that relies on movable blocks, where each block contains no more than a single needle.

FIG. 8 is an exemplary illustration of the needle-substrate unit of varying compositions.

DETAILED DESCRIPTION OF THE INVENTION

A customizable tattoo stamp system in some embodiments can comprise a customizable needle-substrate unit, a charging unit, an image processor unit, and an ink roller. In some embodiments, the tattoo stamp system consists of a pneumatic injection device, which facilitates the transfer of the tattoo from the customizable needle pad into the skin.

The customizable needle-substrate unit is comprised of the substrate and the needles. The substrate can be comprised of stainless steel or a polymer, or any combination thereof. The material that the substrate is comprised of depends upon the area of the skin where the tattoo needs to be made. (e.g., if the tattoo will be printed on a curved area of the body, the substrate can be made of a flexible material to accommodate the curve of the body, such as the upper arm or wrist).

The needles can be comprised of any material that is sufficiently hard and strong. In some embodiments, the microneedle is comprised of stainless steel, nickel, or a polymer, or any combination thereof. The material used to manufacture the needles should be sufficiently stiff to pierce the human skin, and at the same time stiff enough to maintain an aspect ratio of 20:1, meaning that each needle is 20 times as long as it is thick.

Figures 8A, 8B:
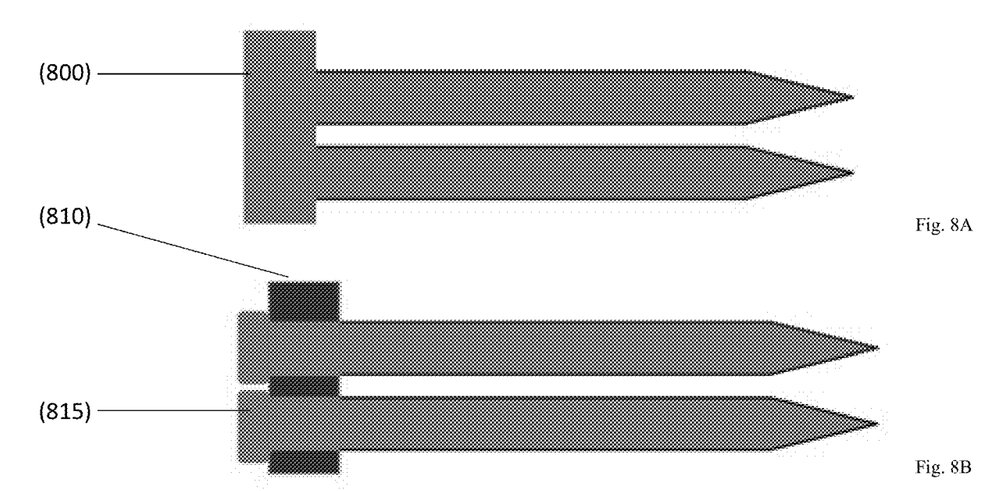
FIG. 8A is an exemplary illustration of a system depicting the hard substrate and continuous metal substrate.
FIG. 8B is an exemplary illustration of a system depicting a hybrid substrate; a soft polymer substrate paired with hard metal needles.
Figure 8C:
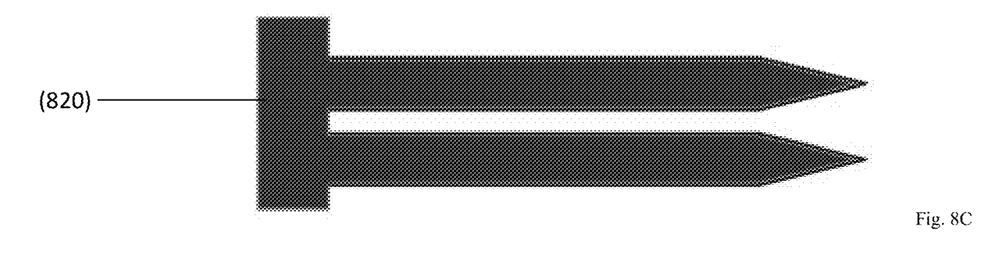
FIG. 8C is an exemplary illustration of a system depicting a soft substrate; continuous polymer substrate, and the needles.
Figure 9:
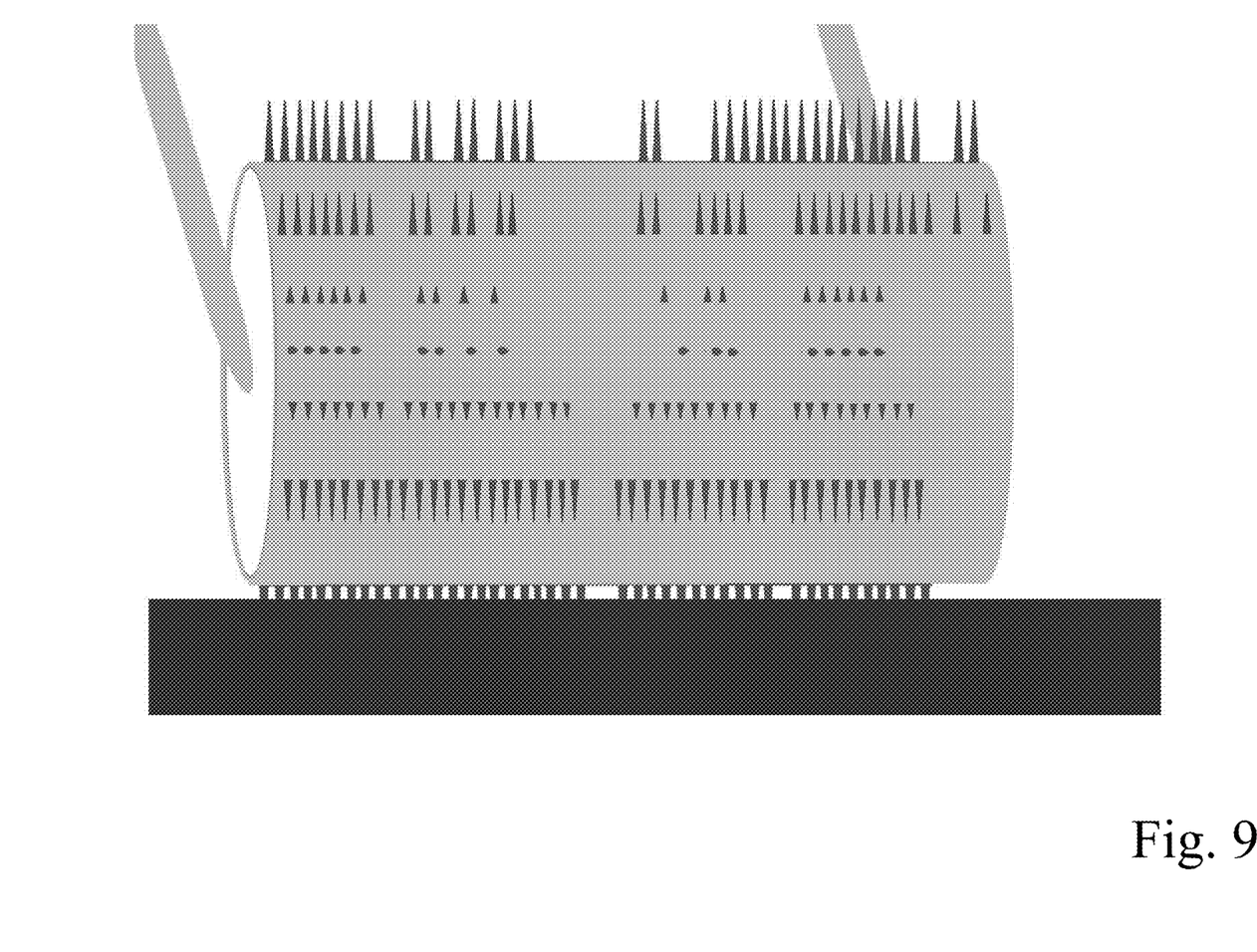
FIG. 9 is an exemplary illustration of a rolling microneedle array where the needles form the image to be printed into the skin.

The substrate and the needles of the customizable needle-substrate unit can be manufactured together or separately depending on the material used to manufacture the needles and the substrate, as depicted by FIG. 8. In some embodiments of the system depicts the hard substrate and continuous metal substrate. Both made of the same hard material (800), e.g., steel or any similar materials. In some embodiments of the system, the substrate and needle can be manufactured from similar materials, which allows to produce them as one piece via commercially available subtractive manufacturing methods such as reactive ion etching (ME). FIG. 8B in some embodiments of the system depicts a hybrid substrate; a soft polymer substrate (810) paired with hard metal needles (815). In some embodiments of the system, the soft polymer substrate can be of the different material than that of the needles, e.g., the needles can be made up of steel, and the substrate can be made up of a soft polymer. FIG. 8C in some embodiments of the system depicts a soft substrate; continuous polymer substrate, and the needles. In some embodiments of the system, the substrate and the needles can be made of the same soft polymer (820), e.g., soft polymer. In some embodiments of the system, a soft substrate can be paired with a pneumatic injection device to ensure even pressure on all needles going into the skin. In this case, the tattoo can be applied to a curved area of the skin. In some embodiments of the system, a soft substrate will not be made of the same material as the needles. It can be made from a commercially available polymer such as Polyethylene, poly (methyl methacrylate), or polydimethylsiloxane.

Figure 1:
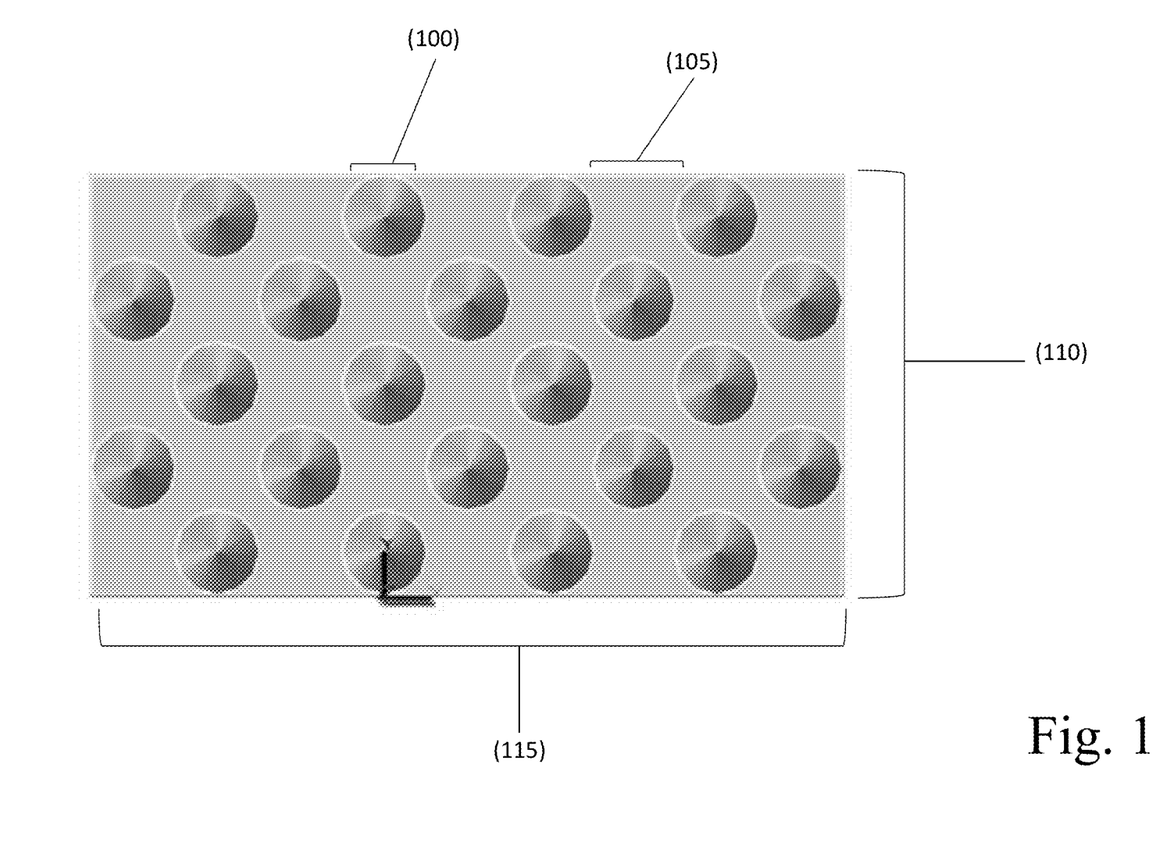
FIG. 1 is an exemplary illustration of the top view of a single movable needle block containing, in this case, eighteen needles.

FIG. 1 depicts the top view of the needle-substrate unit. In some embodiments of the system the diameter of the needles (100) can be from 100 to 250 micrometers, and, in some embodiments of the tattoo stamp, the spacing (105) between the needles can be from 100 to 300 micrometers in both x and y dimensions. In some embodiments of the system, as depicted in the FIGS. 2 and 3 the length of the tip of the needles (200) and (300) can be from 100 to 250 micrometers, and, in some embodiments of the system the needles (205) and (305) can be from 1000 and 2000 micrometers tall, which is the length from the base of the needle up to the tip.

Figure 2:
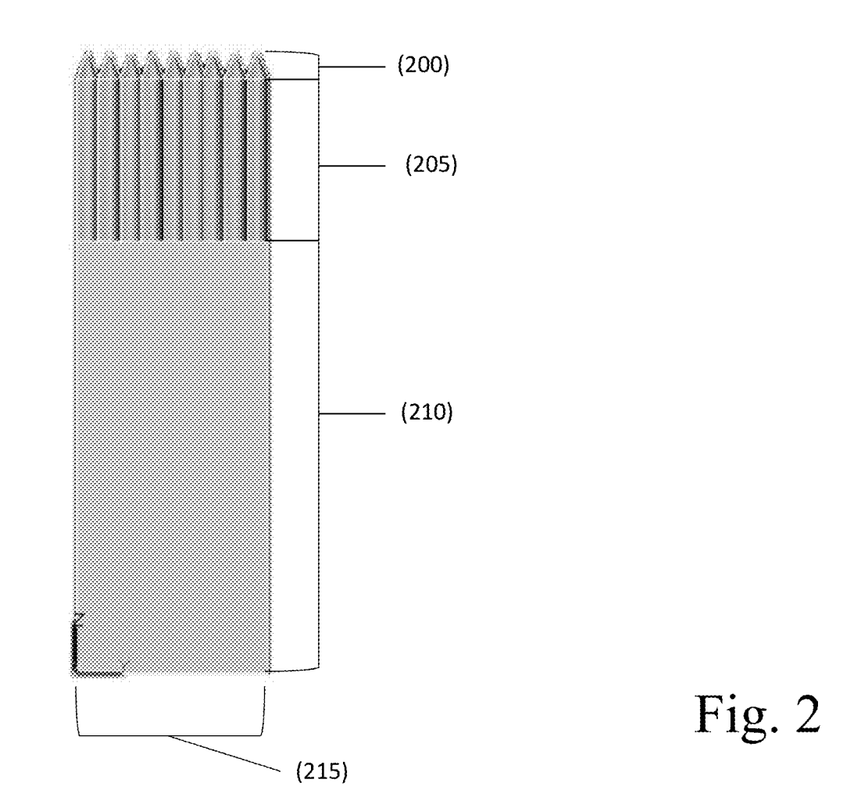
FIG. 2 is an exemplary illustration of a side view of a single movable needle block, containing in this case, eighteen needles.

FIG. 2 depicts a side view of the needle-substrate unit. In some embodiments of the system, as depicted in the FIGS. 1, 2 and 3 the length of the substrate (115), (210), and (320) can be from 0.5 to 4.0 inches, and in some embodiments of the system, the substrate width (110), (215), and (315) can be from 0.5 to 2.0 inches.

Figure 3:
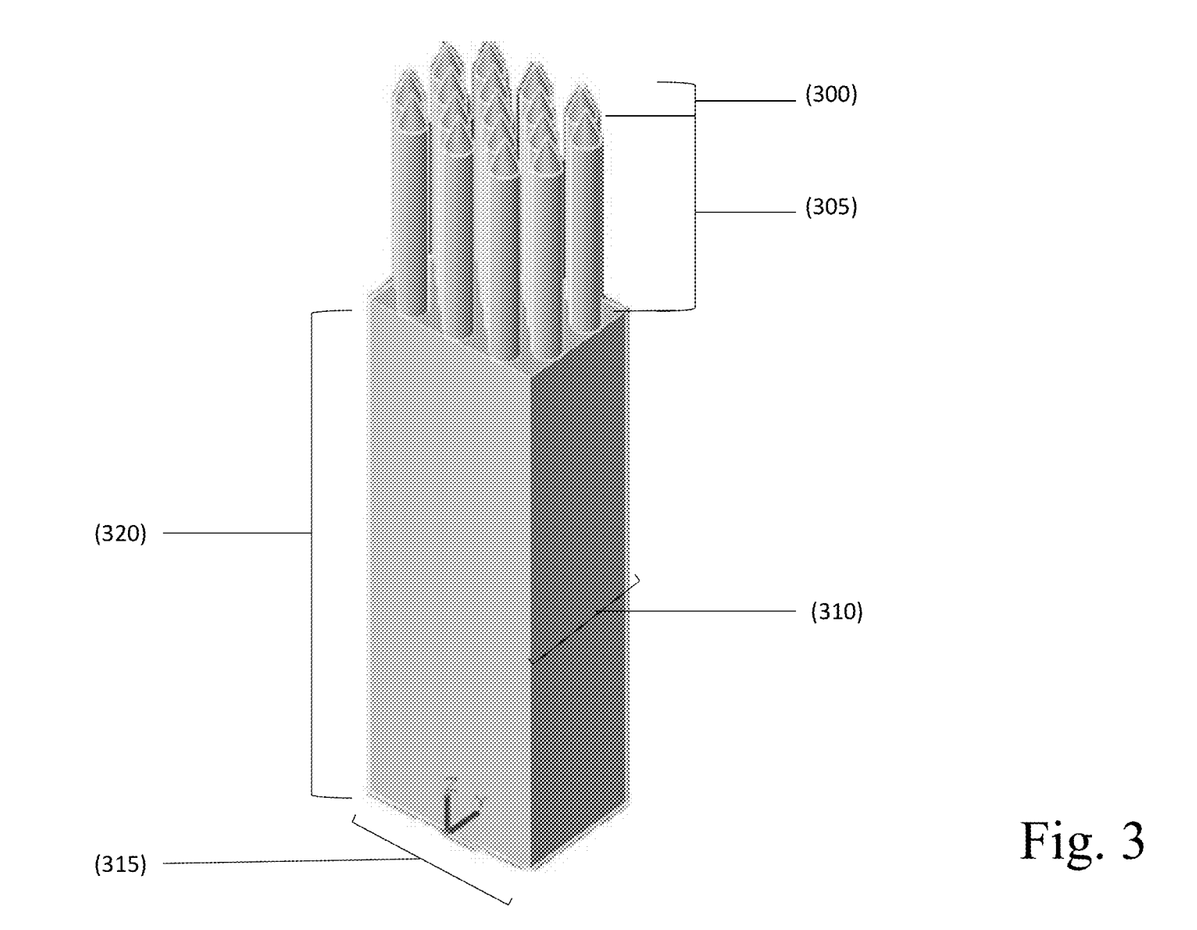
FIG. 3 is an exemplary illustration of an isometric view of a single movable needle block containing, in this case, eighteen needles.

FIG. 3 depicts an isometric view of the needle-substrate unit. In some embodiments of the system, the thickness of the substrate (310) can be from 1000 to 10000 micrometers.

Figure 4A:
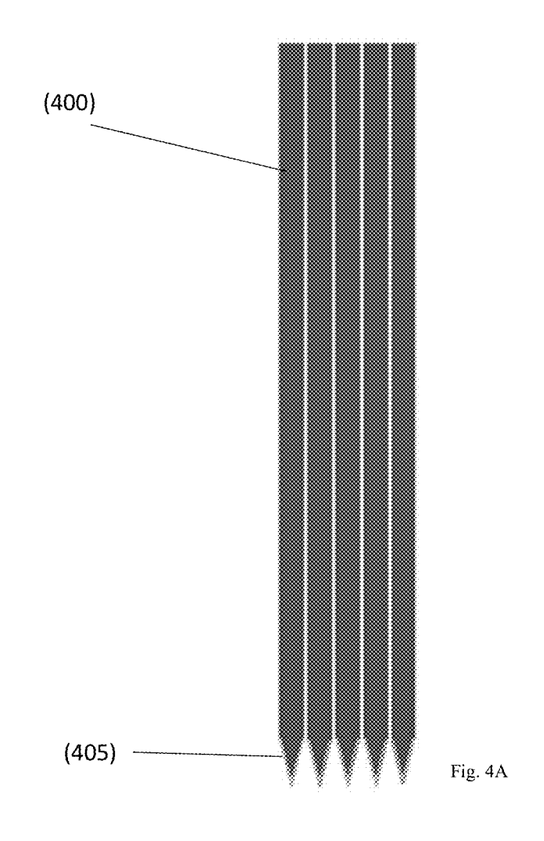
FIG. 4 is an exemplary illustration of an array individual movable needles with tessellating cross sections.
Figure 4B:
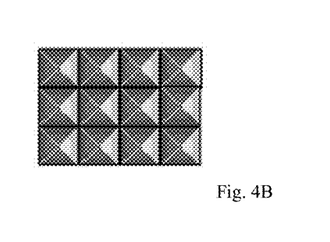

In some embodiments the tip (405) of the needle can be coated with a photoactive polymer used to electrically insulate the microneedles from one and another, as depicted in FIG. 4. FIG. 4 depicts the cross-sectional view of the needles. In some embodiments, the needles do not have to be coated in a photoactive polymer if they are electrically insulated from one another, e.g., if they are separate pieces attached to a plastic substrate. Further, in some embodiments of the system, the needles (400) are composed of stainless steel.

In some embodiments the tattoo stamp system involves multiple steps in the tattooing process, as depicted by FIG. 5, which is discussed in detail below.

Figure 5A:
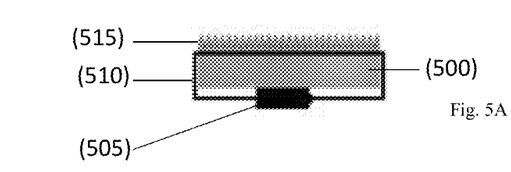
FIG. 5A is an exemplary illustration of a needle and substrate section connected to a power source through a corona wire, also known as a charging unit.

In some embodiments, as depicted by FIG. 5A of FIG. 5, the charging unit is comprising of a power source (505), and a corona wire (510). In some embodiments, the corona wire connected with a power source is used to give a positive charge to the tip of the microneedles (515) coated with a photoactive molecule. Once the needles are positively charged the power source is disconnected (525) and (545) from the rest of the substrate, as depicted by FIG. 5B. The corona wire and the power source can either be embedded in the needle-substrate unit (500) or be placed externally.

Figure 5B:
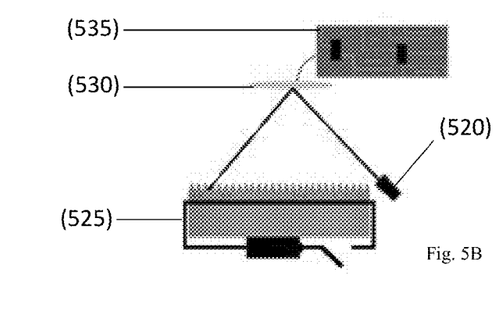
FIG. 5B is an exemplary illustration of an embodiment depicting an image processor, and a charging unit.

In some embodiments the image processing unit can be of two types, one which consists of a microprocessor (535), a laser (520) and a mirror (530), as depicted by FIG. 5B and the other which consists of a microprocessor and a Computer Numerical Control (CNC) laser, which is used in the laser printing. The user loads a two-dimensional image in the microprocessor. The microprocessor acts as a control center for the image processor unit, as depicted in FIG. 5B. In the first case, the laser and its reflection through a mirror is controlled by the microprocessor, as depicted in FIG. 5B. The reflected ray of the laser is used by the microprocessor to trace the two-dimensional image on the customizable needle-substrate unit, as depicted in FIG. 5B. Whereas in the second case the microprocessor controls the CNC laser suspended directly above the needle-substrate unit, to trace the image on the customizable needle-substrate unit.

In some embodiments during the process of tracing the image on the positively charged customizable needle-substrate unit, the areas struck by the laser become negatively charged. Areas not traced over by the laser maintain a positive charge. At the end of this process, the needle-substrate unit bears a negative and a positive charge. The positive charge is represented by a white area, which corresponds to the blank part on the skin whereas the negative charge is represented by a dark area, which corresponds to the inked part of the skin.

Figure 5C:
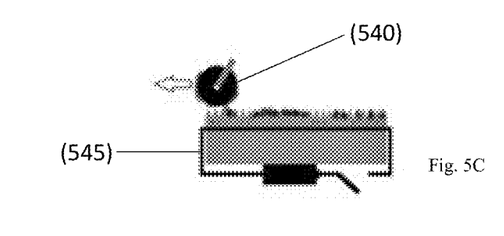
FIG. 5C is an exemplary illustration of an ink loading roller and the needle-substrate section.

In some embodiments, as depicted in FIG. 5C the positively charged ink roller (540) is moved over the entire needle-substrate unit. The negatively charged region of the needle-substrate unit attract the permanent tattoo ink and becomes coated with it. On the opposite, the positively charged part of the customizable needle-substrate unit repels the permanent tattoo ink. At the end of this process the permanent tattoo ink now sits on the needles in the shape of the desired image. The tattoo stamp system can create a multicolor image on the skin by repeating the whole process discussed above with the desired colors each time in order to create a multi-color image.

Figure 5D:
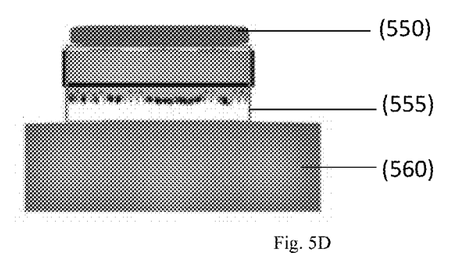
FIG. 5D is an exemplary illustration of a pneumatic injection device in some of the embodiments, and a permanent tattoo ink loaded needle-substrate unit.
Figure 5E:
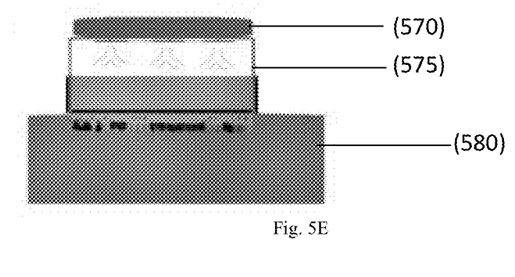
FIG. 5E is an exemplary illustration of an embodiment depicting the transfer of the permanent tattoo ink into the skin using the pneumatic injection device.

In some embodiments the tattoo stamp system can use an injection device to inject the permanent tattoo ink into the skin. The injection device can operate on the pneumatic (550) as depicted by FIG. 5D or mechanical or electrostatic principles. In some embodiments of the system, as depicted by FIG. 5D and FIG. 5E, a pneumatic injection device (550) and (570), which is a sterile unit comprising of an airtight frame (555) and (575) is placed on the skin (560) at the desired location, which is used to inject the permanent tattoo ink placed on the customizable needle-substrate unit at once into the skin (580) at the desired depth, location, and pattern. In some embodiments the needles are attached, facing inward, to the inner side of a pneumatic device similar to a blood pressure cuff. The cuff is placed on a client's body around the area to be tattooed, and pressure is increased to evenly insert the needles into the skin to release the permanent tattoo ink at the desired location. The pneumatic injection device works on a push and pull mechanism, which results in creating a tattoo on the skin on a single use. Once, the ink is injected at the desired location on the skin, the needle-substrate unit is drawn back.

Figure 5F:
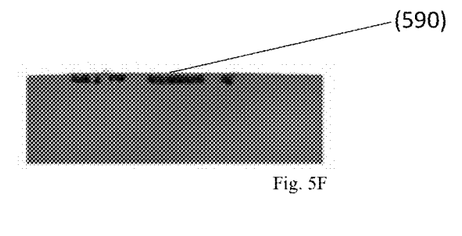
FIG. 5F is an exemplary illustration of the permanent tattoo ink left embedded in the skin in the desired pattern.

In some embodiments, FIG. 5F depicts the permanent tattoo ink left embedded in the skin in the desired pattern (590), once the needle-substrate unit is drawn back. Under this process the needles only have to be in the skin for a fraction of a second to inject the ink, unlike a conventional tattooing process.

Figure 6A:
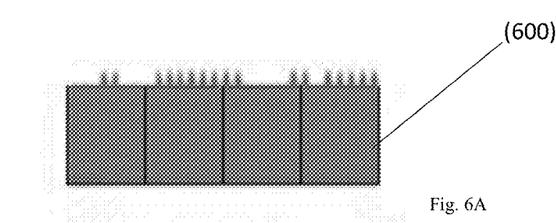
FIG. 6A is an exemplary illustration of a custom needle pad, consisting of numerous blocks individually movable blocks which hold needles whose points form the shape of the desired image.
Figure 6B:
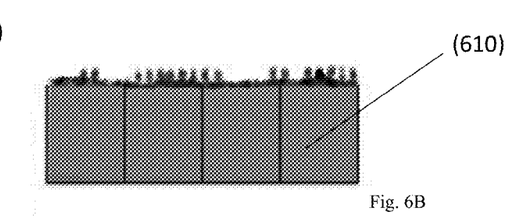
FIG. 6B is an exemplary illustration of an entire needle pad coated with the permanent tattoo ink.
Figure 6C:
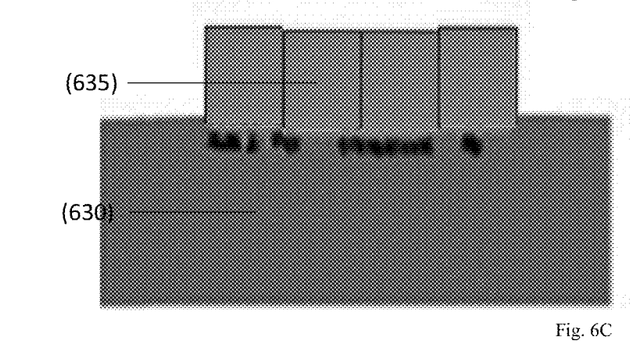
FIG. 6C is an exemplary illustration of the permanent tattoo ink loaded needle pad embedded in the skin, showing that the blocks can move independently to allow the needles to penetrate to the same depth in different regions of the skin, even as the skin depresses.
Figure 6D:
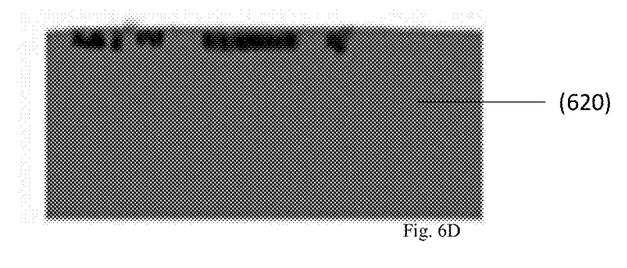
FIG. 6D is an exemplary illustration of the permanent tattoo ink left in the skin in the desired pattern.
Figure 7A:
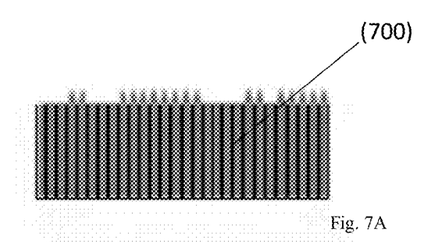
FIG. 7A is an exemplary illustration of a custom needle pad, consisting of numerous blocks individually movable blocks which hold needles whose points form the shape of the desired image.
Figure 7B:
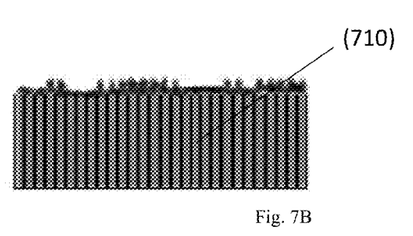
FIG. 7B is an exemplary illustration of an entire needle pad coated with the permanent tattoo ink.
Figure 7C:
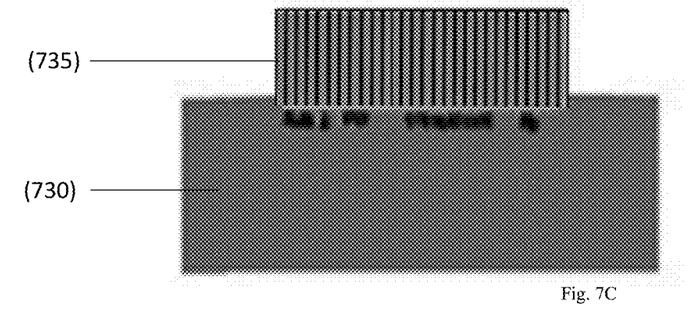
FIG. 7C is an exemplary illustration of the permanent tattoo ink loaded needle pad embedded in the skin, showing that the blocks can move independently to allow the needles to penetrate to the same depth in different regions of the skin, even as the skin depresses.
Figure 7D:
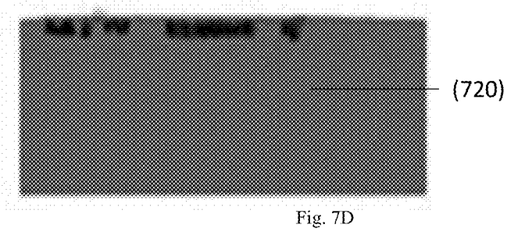
FIG. 7D is an exemplary illustration of the permanent tattoo ink left in the skin in the desired pattern.

In some embodiments the tattoo stamp system can use a mechanical force of the hand to inject the permanent tattoo ink into the skin. The mechanical principle of injection can utilize two approaches. In one type of approach, which is depicted by FIG. 6A of FIG. 6, a custom needle pad (600) is produced with the needles in the shape of the desired image. The entire custom needle pad is coated with the permanent tattoo ink (610), as depicted by FIG. 6B. Each ink coated needle corresponds to a pixel in the image. FIG. 6C depicts in some embodiments of a system; an ink loaded needle pad (635) embedded in the skin (630). The ink loaded needle pad in manually pushed into the skin. FIG. 6D depicts in some embodiments of a system the permanent tattoo ink left on the skin (620) in the desired pattern, as the pad is withdrawn from the skin. The customizable needle pad can be disposed of depending on the material used to manufacture the needle-substrate unit.

In some embodiments of the tattoo stamp system, another type of the mechanical injection method can be comprised of a needle pad wrapped around a cylindrical roller, with the needles pointing outward. The roller is rolled over the skin, evenly pressing the needles into the epidermis at the desired depth and releasing the permanent tattoo ink into the skin, eventually creating an image at the desired location.

In some embodiments of the tattoo stamp system, a multicolor image can be created on the skin by repeating the whole process discussed above with the desired colors each time in order to create a multi-color image.

While preferred embodiments of the present invention have been shown and described herein, it will be obvious to those skilled in the art that such embodiments are provided by way of example only Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A customizable tattoo stamp system comprising:
   a customizable needle-substrate unit further comprising an array of individual movable blocks, each of the individual movable blocks including one or more closely spaced needles; and
   an injection device that operates using mechanical principles to press the needles into a target's skin, allowing for permanent tattoo ink to be transferred into the skin in a desired pattern to create a permanent tattoo, wherein the injection device comprises an array of electromagnets configured to individually exert force on specific blocks of the individual movable blocks.

2. The system of claim 1 wherein the needles are either fabricated as a single component with the individual movable blocks or are bound to the individual movable blocks.

3. A method comprising:
selectively arranging an array of individual movable blocks including one or more closely spaced needles so that the needles form a two dimensional image;
coating the array of individual movable blocks with tattoo ink; and
transferring, using an injection device operating on mechanical principles and comprising an array of electromagnets configured to individually exert force on specific blocks of the individual movable blocks, tattoo ink through the needles to a target's skin to create a permanent tattoo depicting the two dimensional image such that the tattoo ink transferred through each needle forms a pixel of the two dimensional image.

4. The method of claim 3 wherein each block contains a number of holes, and wherein each needle is placed into one of the number of holes in a manner such that the needles form the image to be injected into the skin.

5. The method of claim 3 wherein each individual movable block is fabricated so that the needles are part of the individual movable block.

6. The method of claim 5 wherein each needle and individual movable block constitutes a single unit so that a bundle of needle and block units are held in compression.

7. The method of claim 3 wherein the using the injection device further comprises selectively injecting only those individual movable blocks that contain needles that are part of a desired image.

8. A method comprising the steps of coating an array of needles with a pattern of permanent tattoo ink and transferring the pattern into a target's skin, wherein the method further comprises a step of tracing a two-dimensional image onto the needle array using a microprocessor, a laser and a mirror, or a computer numerical control laser and a microprocessor.

9. The method of claim 8 wherein the coating step further comprises coating the needle array by charge using a corona wire and a power source connected to the needle array.

10. The method of claim 8 wherein the coating step further comprises using a positive charged ink roller to coat the array of needles with the pattern of permanent tattoo ink.

* * * * *